United States Patent [19]

Hofer

[11] Patent Number: 4,925,847

[45] Date of Patent: * May 15, 1990

[54] 6-THIOXANTHINES

[75] Inventor: Peter Hofer, Liestal, Switzerland

[73] Assignee: Euroceltique, S.A., Luxembourg

[*] Notice: The portion of the term of this patent subsequent to Dec. 1, 2004 has been disclaimed.

[21] Appl. No.: 78,545

[22] Filed: Jul. 28, 1987

Related U.S. Application Data

[63] Continuation-in-part of Ser. No. 699,254, Feb. 7, 1985, Pat. No. 4,710,503.

[30] Foreign Application Priority Data

Aug. 2, 1986 [GB] United Kingdom ............... 8618931

[51] Int. Cl.$^5$ .................. C07D 473/06; A61K 31/52
[52] U.S. Cl. .................. 514/263; 544/267; 544/273; 514/262
[58] Field of Search .............. 544/276, 277, 273, 267; 514/263

[56] References Cited

U.S. PATENT DOCUMENTS 3,900,474 8/1979 Ginger et al. ............... 544/267
4,546,182 10/1989 Kjellin et al. ............... 544/267
4,710,503 12/1987 Hofer ............... 544/267

Primary Examiner—Nicholas S. Rizzo
Attorney, Agent, or Firm—Steinberg & Raskin

[57] ABSTRACT

A 6-thioxanthine of general formula I or a pharmaceutically acceptable salt thereof

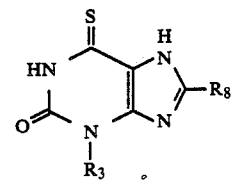

wherein $R_3$ is a $C_2$ to $C_6$ alkyl, a $C_3$ to $C_7$ cycloalkyl group or a $C_4$ to $C_8$ cycloalkylalkyl group and $R_8$ is a $C_1$ to $C_6$ alkyl, a $C_3$ to $C_7$ cycloalkyl group or a $C_4$ to $C_8$ cycloalkylalkyl group provided that when $R_3$ is an ethyl, n-propyl or n-butyl group, $R_8$ is a $C_3$ to $C_6$ alkyl, a $C_3$ to $C_7$ cycloalkyl group or a $C_4$ to $C_8$ cycloalkylalkyl group.

These 3,8-disubstituted-6-thioxanthines have enhanced bronchodilator activity.

11 Claims, No Drawings

6-THIOXANTHINES

CROSS REFERENCE TO RELATED APPLICATION

This is a continuation-in-part of co-pending application Ser. No. 699,254, filed Feb. 7, 1985, now U.S. Pat. No. 4,710,503.

The present invention relates to 6-thioxanthines and in particular to 3,8-disubstituted-6-thioxanthines having bronchodilator activity and which are useful in the treatment of chronic obstructive airway disease.

Brit. J. Pharmacol., 1961, 17, 196 –207 describes 3-isobutyl-6-thioxanthine. This compound (Compound No. 30 in Table 4) was tested, along with 6-thiotheophyllines (1,3-disubstituted-6-thioxanthines), 6-thiotheobromines (3,7-disubstituted-6-thioxanthines) and 6-thiocaffeines (1,3,7-trisubstituted-6-thioxanthines), for bronchodilator activity. The authors concluded, from these experiments, that only 6-thiotheophyllines were of any potential therapeutic interest.

U.S. Pat. No. 4,710,503 describes certain 6-thioxanthines having bronchodilator activity in which the 3-nitrogen is substituted by an ethyl, n-propyl or n-butyl group, whilst the 8-carbon is either unsubstituted or substituted by a methyl or ethyl group. The preferred materials are said to be 3-ethyl-6-thioxanthine and 3-n-propyl-6-thioxanthine.

It has now been found that 6-thioxanthines in which both the 3 and the 8 positions are substituted by alkyl or cycloalkyl 9roups exhibit greater bronchodilator activity than 6-thioxanthines in which only the 3 position is substituted.

U.S. Pat. No. 4,546,182 describes 3,8-dialkylxanthines and their bronchodilator activity. The present inventors have also found that the replacement of the 6-oxo group, of the compounds described in U.S. Pat. No. 4,546,182, with a 6-thio group, enhances bronchodilator activity.

It is an object of the present invention to provide 3,8-disubstituted-6-thioxanthines which have an enhanced bronchodilator effect.

Other objects and advantages of the present invention will become apparent from the following detailed description thereof.

According to the present invention, there is provided a 6-thioxanthine of general formula I or a pharmaceutically acceptable salt thereof

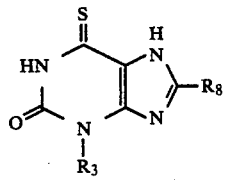

I wherein $R_3$ is a $C_2$ to $C_6$ alkyl, a $C_3$ to $C_7$ cycloalkyl group or a $C_4$ to $C_8$ cycloalkylalkyl group, and $R_8$ is a $C_1$ to $C_6$ alkyl, a $C_3$ to $C_7$ cycloalkyl group or a $C_4$ to $C_8$ cycloalkylalkyl group provided that when $R_3$ is an ethyl, n-propyl or n-butyl group, $R_8$ is a $C_3$ to $C_6$ alkyl, a $C_3$ to $C_7$ cycloalkyl group or a $C_4$ to $C_8$ cycloalkylalkyl group.

Preferably $R_3$ is a $C_2$ to $C_5$ alkyl or a $C_3$ to $C_5$ cycloalkyl group and $R_8$ is a $C_2$ to $C_5$ alkyl or $C_3$ to $C_5$ cycloalkyl group. Preferably $R_3$ and $R_8$, when combined, contain between 5 and 8 carbon atoms. Most preferably $R_3$ is a $C_2$ to $C_5$ alkyl group, $R_8$ is a $C_3$ to $C_5$ cycloalkyl group, and $R_3$ and $R_8$, when combined, contain between 5 and 8 carbon atoms. Thus $R_3$ may be a hexyl, methylpentyl, dimethylbutyl or ethylbutyl group, but is preferably an ethyl, propyl, cyclopropyl, butyl, cyclobutyl, pentyl, cyclopentyl, methylbutyl, or dimethylpropyl group, whilst $R_8$ may be methyl, hexyl, methylpentyl, dimethylbutyl or ethylbutyl group but is preferably an ethyl, propyl, cyclopropyl, butyl, cyclobutyl, pentyl, cyclopentyl, methylbutyl or dimethylpropyl group.

In a particularly preferred embodiment of the present invention, $R_3$ is an ethyl, n-propyl or n-butyl group and $R_8$ is a cyclopropyl or cyclobutyl group.

The compounds of the present invention have increased bronchodilator activity when compared with both (i) the equivalent xanthine, (oxygen replaces sulphur), and (ii) the 3-substituted-6-thioxanthine obtained by replacing the 8-alkyl or cycloalkyl group of a compound according to this invention by a hydrogen atom.

Thus 3-n-propyl-8-cyclobutyl-6-thioxanthine has an enhanced bronchodilator effect compared with both 3-n-propyl-8-cyclobutylxanthine and 3-n-propyl-6-thioxanthine.

Certain of these novel 6-thioxanthines may also exhibit other therapeutic activities, for example anti-inflammatory activity.

The present invention includes pharmaceutically acceptable salts of compounds of general formula I with pharmaceutically acceptable bases. The term "pharmaceutically acceptable salts" means salts, the cations of which are relatively innocuous to the animal organism when used in therapeutic doses so that the beneficial pharmacological properties of the parent compounds of general formula I are not impaired by side effects ascribable to the cations. Suitable salts include alkali metal salts, e.g. sodium and potassium, ammonium salts and amine salts, such as glycine, lysine, ethylene diamine, choline, diethanolamine, triethanolamine, octadecylamine, diethylamine, triethylamine, 1-amino-2-propanol, 2-amino-2-(hydroxymethyl)- propane-1,3-diol and 1-(3,4-dihydroxyphenyl)-2-isopropyl- aminoethanol.

According to a further aspect of the present invention there is provided a pharmaceutical composition for use in the treatment of chronic obstructive airway disease, comprising a 6-thioxanthine of general formula I or a pharmaceutically acceptable salt thereof wherein $R_3$ and $R_8$ are as hereinbefore defined in conjunction with a pharmaceutically acceptable diluent or carrier.

In such compositions, the present thioxanthines may be the sole active ingredient. Alternatively, they may be combined with such drug substances as beta-agonists (e.g. salbutamol, terbutaline, rimiterol and fenoterol), calcium ion antagonists (e.g. nifedipine, verapamil and diltiazem), and mucolytic agents (e.g. ambroxol and bromhexine).

In clinical practice, the compounds of the present invention may be administered rectally, nasally, sublingually, by injection, by inhalation or, which is preferred, orally. The compounds may be administered as pharmaceutical compositions in solid, semi-solid, liquid or capsule form. Usually the active ingredient will comprise between 0.1 and 99% (by wt) of the pharmaceutical composition, especially between 0.5 and 20% (by wt) for compositions intended for injection and between 0.1 and 50% (by wt) for compositions intended for oral administration. Solid, oral dosage forms according to this invention may be prepared by combining the active ingredient with excipients and diluents such as (a) Binders, such as cellulose and its derivatives, starches, polyvinylpyrrolidone, natural gums, gelatin, (b) Glidants, such as talc and fumed silica, (c) Lubricants, such as stearate salts, PEG waxes, (d) Disintegrants, such as starch and its derivatives, microcrystalline cellulose, croscarmellose sodium, low substituted hydroxypropyl cellulose, cross linked polyvinylpyrrolidone, (e) Diluents, such as sugars and sugar alcohols, (f) Colorants, Flavorants and Sweeteners.

Advantageously, the solid, oral dosage form may have a protective coating which may, for example, serve to mask the taste of the active ingredient.

In addition to the above materials, in a further aspect of the present invention, the pharmaceutical composition may also contain substances suitable for the formation of a controlled release formulation. In particular, the composition may contain a hydrated, water soluble, hydroxyalkyl cellulose, especially hydroxyethyl cellulose, and a higher aliphatic alcohol, especially cetostearyl alcohol, as described in British Pat. No. 1,405,088 (equivalent to U.S. Pat. No. 3,965,256 and U.S. Pat. No. 4,235,870), the contents of which documents are herein incorporated by way of reference. Soft gelatin capsules consisting of gelatin and, for example, glycerol as a plasticiser, may contain the active ingredient in an oil, such as sesame oil, olive oil or arachis oil, or admixed with a PEG wax. Hard gelatin capsules may contain granules of the active ingredient mixed with suitable excipients and diluents.

Liquid, oral dosage forms may be elixirs, syrups or suspensions. Such forms may contain sweeteners, flavorants, preservatives, emulsifying agents and dispersing agents.

Parenteral forms may be an aqueous solution or suspension of the active ingredient, optionally containing stabilising agents and/or buffer substances.

For inhalation purposes, the active ingredient may be delivered via an aerosol or a nebuliser. The active ingredient may be present as a solid, a suspension or a solution.

The dosage of the present 6-thioxanthines that will be administered to a patient will vary within wide limits and will depend on various factors such as the type of patient and the disease to be treated. A suitable oral dosage may be 25 to 500 mg given 1 to 4 times a day while a suitable parenteral dose may be 10 to 250 mg also given 1 to 4 times per day.

The compounds of general formula I may be prepared by thionation of the corresponding 6-oxo compounds. This may be performed, for example, by treatment of the 6-oxo compounds with phosphorus pentasulphide in pyridine. This thionation is suitably carried out by treating a suspension of the 6-oxo compound in pyridine with a molar excess of phosphorus pentasulphide (e.g. from 1.25 to 2.00 moles of $P_2S_5$ per mole of 6-oxo compound).

The starting 6-oxo compounds may be prepared from 4,5-diamino -3-substituted pyrimidin-2,6-diones in the manner described in U.S. Pat. No. 4,546,182. Alternatively they may be prepared by other standard acylation procedures followed by ring closure in alkaline solution.

6-Thioxanthines according to this invention, methods of preparing such thioxanthines and pharmaceutical compositions containing such thioxanthines will now be described by way of example only.

EXAMPLE 1

3-(2-Methylbutyl)-8-ethyl-6-thioxanthine 3-(2-Methylbutyl)-8-ethylxanthine (13.33 gm) and phosphorus pentasulphide (14.23 gm) were refluxed in pyridine (190 ml) at a bath temperature of 140° C. After 4.5 hr, the brown solution was cooled to 10° C. and 2N sodium hydroxide (70 ml) was added. The pyridine was removed in vacuo from the suspension.

The residue was suspended in water (100 ml), collected and washed with cold water. The crude 6-thioxanthine was dissolved in 1N sodium hydroxide 100 ml) and the solution was treated with 0.3 gm of charcoal, filtered, and acidified with 5N hydrochloric acid (co pH 2 -3) . The solid obtained was collected, washed with water and dried. The crude 6-thioxanthine (11.4 gm) was then dissolved in chloroform (200 ml) and filtered through a silica gel column. The chloroform was then evaporated and the residue was dissolved in hot isopropanol (100 ml), treated with 0.3 gm of charcoal, filtered and crystallised. 9.75 gm of crystalline 6-thioxanthine (68.7% yield, mp 232°-4° C.) was obtained.

Elemental analysis for $C_{12}H_{18}N_4OS$,
Calc: C 54.11%, H 6.81%, N 21.03%, S 12.04%
Found: C 54.0%, H 7.02%, N 21.03%, S 11.91%

EXAMPLE 2

3-Ethyl-8-n-butyl-6-thioxanthine

This compound was prepared, as described in Example 1, starting from 3-ethyl-8-n-butylxanthine. Crystalline 6-thioxanthine (70% yield, mp 215°-16° C.) was obtained.

Elemental analysis for $C_{11}H_{16}N_4OS$,
Calc: C 52.37%, H 6.39%, N 22.21%, S 12.70%
Found: C 52.33%, H 6.58%, N 22.15%. S 12.73%

EXAMPLE 3

3-n-Propyl-8-n-butyl-6-thioxanthine

This compound was prepared, as described in Example 1, starting from 3-n-propyl-8-n-butylxanthine. Crystalline 6-thioxanthine (83% yield, mp 199°-201° C.) was obtained.

Elemental analysis for $C_{12}H_{18}N_4OS$,
Calc: C 54.11%, H 6.81%, N 21.03%, S 12.04%
Found: C 53.98%, H 7.07%, N 20.92%, S 11.87%

EXAMPLE 4

3-n-Propyl-8-n-pentyl-6-thioxanthine

This compound was prepared, as described in Example 1, starting from 3-n-propyl-8-n-pentylxanthine. Crytalline 6-thioxanthine (86% yield, mp 183°-5° C.) was obtained.

Elemental analysis for $C_{13}H_{20}N_4OS$,
Calc: C 55.70%, H 7.19%, N 19.98%, S 11.43%
Found: C 55.48%, H 7.40%, N 20.01%, S 11.21%

EXAMPLE 5

3-n-Propyl-8-cyclopropyl-6-thioxanthine

This compound was prepared, as described in Example 1, starting from 3-n-propyl-8-cyclopropylxanthine.

Crystalline 6-thioxanthine (76% yield, mp 261°-4° C.) was obtained.
Elemental analysis for $C_{11}H_{14}N_4OS$,
Calc: C 52.70%, H 5.64%, N 22.39%
Found: C 52.62%, H 5.80%, N 22.39%

EXAMPLE 6

3-n-Propyl-8-cyclobutyl-6-thioxanthine

This compound was prepared, as described in Example 1, starting from 3-n-propyl-8-cyclobutylxanth. Crystalline 6-thioxanthine (70% yield, mp 227°-8° C.) was obtained.
Elemental analysis for $C_{12}H_{16}N_4OS$,
Calc: C 54.55%, H 6.10%, N 21.20%, S 12.13%
Found: C 54.56%, H 6.38%, N 21.21%, S 12.30%

EXAMPLE 7

3-Isobutyl-8-butyl-6-thioxanthine

This compound was prepared, as described in Example 1, starting from 3-isobutyl-8-butylxanthine. Crystalline 6-thioxanthine (81% yield, mp 232°-4° C.) was obtained.
Elemental analysis for $C_{13}H_{20}N_4OS$,
Calc: C 55.70%, H 7.19%, N 19.98%, S 11.44%
Found: C 55.56%, H 7.40%, N 19.93%, S 11.19%

EXAMPLE 8

3-n-Pentyl-8-ethyl-6-thioxanthine

This compound was prepared, as described in Example 1, starting from 3-n-pentyl-8-ethylxanthine. Crystalline 6-thioxanthine (81% yield, mp 193°-7° C.) was obtained.
Elemental analysis for $C_{12}H_{18}N_4OS$,
Calc: C 54.12%, H 6.81%, N 21.04%
Found C 54.07%, H 6.88%, N 21.19%

EXAMPLE 9 3-Isopentyl-8-ethyl-6-thioxanthine

This compound was prepared, as described in Example 1, starting from 3-isopentyl-8-ethylxanthine. Crystalline 6-thioxanthine (68.9% yield, mp 210°-11° C.) was obtained.
Elemental analysis for $C_{12}H_{18}N_4OS$,
Calc: C 54.11%, H 6.81%, N 21.03%, S 12.04%
Found: C 53.96%, H 7.10%, N 20.81%, S 11.81%

Choline salts of the above thioxanthines were prepared according to the method described in K. R. H. Wooldridge etal, J.Chem. Soc., 1962, 1863.

EXAMPLE 10

Tablets having the following composition were prepared,

| | |
|---|---|
| 3-n-Propyl-8-n-butyl-6-thioxanthine (Example 3) | 50 mg |
| Hydroxypropylmethylcellulose (4000 cps) | 100 mg |
| Lactose | 100 mg |
| Talc | 10 mg |
| Magnesium stearate | 5 mg |

EXAMPLE 11

Controlled release tablets having the following composition were prepared,

| | |
|---|---|
| 3-n-Propyl-8-cyclobutyl-6-thioxanthine (Example 6) | 75 mg |
| Cetostearyl alcohol | 30 mg |
| Hydroxyethyl cellulose | 15 mg |
| Lactose | 120 mg |
| Talc | 15 mg |
| Magnesium stearate | 5 mg |

EXAMPLE 12

Suppositories having the following composition were prepared,

| | |
|---|---|
| 3-n-Propyl-8-n-butyl-6-thioxanthine (Example 3) | 50 mg |
| Suppository Base | 1944 mg |
| Antioxidant | 6 mg |

EXAMPLE 13

An aerosol for inhalation was prepared containing

| | |
|---|---|
| 3-n-Propyl-8-n-butyl-6-thioxanthine (Example 3) | 2.0 g |
| Surfactant | 1.0 g |
| Propellant 11 | 25 g |
| Propellant 12 | 75 g |

Pharmacological Tests

Isolated Guinea Pig Trachea

The test compound was dissolved in DMSO. Guinea pig isolated trachealis muscle was mounted in a bath containing Krebs solution (pH 7.4) maintained at 37.5? C. and bubbled with carbogen (95% $O_2$, 5% $CO_2$).

Tension changes were recorded isometrically using force displacement transducers in conjunction with potentiometric pen recorders.

The ability of the test compounds to relax airways muscle was investigated by the construction of cumulative concentration effect curves. Each concentration of the test compound was allowed to equilibrate with the tissue for 5 minutes before a concentration increment (ten-fold) was made.

In each tissue of 3-alkyl-8-alkyl(or cycloalkyl)-6-thioxanthine, 3-alkyl-6-thioxanthine or 3-alkyl-8-alkyl(or cycloalkyl) xanthine was compared with theophylline (as the standard). In one half of the tissues the theophylline was applied first, in the other half the theophylline was applied second. In this way the effect of order of compound administration on potency was minimised.

Results are given in Tables 1-9.

TABLE 1

| Compound | In Vitro Activity |
|---|---|
| Theophylline | 1 |
| 3-Ethyl-6-thioxanthine | 3.2 |
| 3-Ethyl-8-n-butylxanthine | 8.2 |
| 3-Ethyl-8-n-butyl-6-thioxanthine (Example 2) | 55.0 |

TABLE 2

| Compound | In Vitro Activity |
|---|---|
| Theophylline | 1 |
| 3-n-Propyl-6-thioxanthine | 5.1 |
| 3-n-Propyl-8-n-butylxanthine | 8.5 |
| 3-n-Propyl-8-n-butyl-6-thioxanthine (Example 3) | 43.7 |

TABLE 3

| Compound | In Vitro Activity |
| --- | --- |
| Theophylline | 1 |
| 3-n-Propyl-6-thioxanthine | 5.1 |
| 3-n-Propyl-8-n-pentyl-6-thioxanthine (Example 4) | 33.1 |

TABLE 4

| Compound | In Vitro Activity |
| --- | --- |
| Theophylline | 1 |
| 3-n-Propyl-6-thioxanthine | 5.1 |
| 3-n-Propyl-8-cyclopropylxanthine | 7.1 |
| 3-n-Propyl-8-cyclopropyl-6-thioxanthine (Example 5) | 433.0 |

TABLE 5

| Compound | In Vitro Activity |
| --- | --- |
| Theophylline | 1 |
| 3-n-Propyl-6-thioxanthine | 5.1 |
| 3-n-Propyl-8-cyclobutylxanthine | 8.9 |
| 3-n-Propyl-8-cyclobutyl-6-thioxanthine (Example 6) | 243.6 |

TABLE 6

| Compound | In Vitro Activity |
| --- | --- |
| Theophylline | 1 |
| 3-Isobutyl-6-thioxanthine | 14.1 |
| 3-Isobutyl-8-n-butyl-6-thioxanthine (Example 7) | 40.9 |

TABLE 7

| Compound | In Vitro Activity |
| --- | --- |
| Theophylline | 1 |
| 3-(2-Methylbutyl)-8-ethylxanthine | 4.4 |
| 3-(2-Methylbutyl)8-ethyl-6-thioxanthine (Example 1) | 48.2 |

TABLE 8

| Compound | In Vitro Activity |
| --- | --- |
| Theophylline | 1 |
| 3-n-Pentyl-8-ethylxanthine | 6.7 |
| 3-n-Pentyl-8-ethyl-6-thioxanthine (Example 8) | 15.4 |

TABLE 9

| Compound | In Vitro Activity |
| --- | --- |
| Theophylline | 1 |
| 3-Isopentyl-8-ethyl-6-thioxanthine (Example 9) | 42.2 |

What is claimed:

1. A compound selected from the group consisting of 3-(2-methylbutyl)-8-ethyl-6-thioxanthine, 3-ethyl-8-n-butyl-6-thioxanthine, 3-n-propyl-8-n-butyl-6-thioxanthine, 3-n-propyl-8-n-pentyl-6-thioxanthine, 3-n-propyl-8-cyclopropyl-6-thioxanthine, 3-n-propyl-8-cyclobutyl-6-thioxanthine 3-isobutyl-8-n-butyl-6-thioxanthine 3-n-pentyl-8-ethyl-6-thioxanthine and 3-isopentyl-8-ethyl-6-thioxanthine, and pharmaceutically acceptable salts thereof.

2. The compound of claim 1 wherein said compound is 3-(2-methylbutyl)-8-ethyl-6-thioxanthine or a pharmaceutically acceptable salt thereof.

3. The compound of claim 1 wherein said compound is 3-ethyl-8-n-butyl-6-thioxanthine or a pharmaceutically acceptable salt thereof.

4. The compound of claim 1 wherein said compound is 3-n-propyl-8-n-butyl-6-thioxanthine or a pharmaceutically acceptable salts thereof.

5. The compound of claim 1 wherein said compound is 3-n-propyl-8-n-pentyl-6-thioxanthine or a pharmaceutically acceptable salt thereof.

6. The compound of claim 1 wherein said compound is 3-n-propyl-8-cyclopropyl-6-thioxanthine or a pharmaceutically acceptable salt thereof.

7. The compound of claim 1 wherein said compound is 3-n-propyl-8-cyclopropyl-6-thioxanthine or a pharmaceutically acceptable salt thereof.

8. The compound of claim 1 wherein said compound is 3-isobutyl-8-n-butyl-6-thioxanthine or a pharmaceutically acceptable salt thereof.

9. The compound of claim 1 wherein said compound is 3-n-pentyl-8-ethyl-6-thioxanthine or a pharmaceutically acceptable salt thereof.

10. The compound of claim 1 wherein said compound is 3-isopentyl-8-ethyl-6-thioxanthine or a pharmaceutically acceptable salt thereof.

11. A pharmaceutical composition for use in the treatment of chronic obstruction airway disease comprising a 6-thioxanthine or a pharmaceutically acceptable salt thereof according to claim 1 in conjunction with a pharmaceutically acceptable diluent or carrier.

* * * * *